United States Patent
Schulz et al.

(10) Patent No.: US 10,029,120 B2
(45) Date of Patent: Jul. 24, 2018

(54) SYSTEM FOR PLANNING RADIATION TREATMENT THERAPY

(71) Applicant: KONINKLIJKE PHILIPS N.V., Eindhoven (NL)

(72) Inventors: Heinrich Schulz, Hamburg (DE); Michael Grass, Buchholz in der Nordheide (DE); Joerg Sabczynski, Norderstedt (DE); Torbjorn Vik, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 785 days.

(21) Appl. No.: 14/383,122

(22) PCT Filed: Feb. 26, 2013

(86) PCT No.: PCT/IB2013/051535
§ 371 (c)(1),
(2) Date: Sep. 5, 2014

(87) PCT Pub. No.: WO2013/144736
PCT Pub. Date: Oct. 3, 2013

(65) Prior Publication Data
US 2015/0018596 A1   Jan. 15, 2015

Related U.S. Application Data

(60) Provisional application No. 61/615,375, filed on Mar. 26, 2012.

(51) Int. Cl.
*A61N 5/00* (2006.01)
*A61N 5/10* (2006.01)
(Continued)

(52) U.S. Cl.
CPC ............ *A61N 5/1031* (2013.01); *A61B 5/061* (2013.01); *A61N 5/1037* (2013.01);
(Continued)

(58) Field of Classification Search
CPC .. A61N 5/1031; A61N 5/1037; A61N 5/1067; A61N 5/1077
(Continued)

(56) References Cited

U.S. PATENT DOCUMENTS 6,320,935 B1   11/2001   Shinar et al.
7,476,235 B2   1/2009    Diederich et al.
(Continued)

FOREIGN PATENT DOCUMENTS

WO   2011080606 A1   7/2011
WO   2011098926 A1   8/2011
(Continued)

OTHER PUBLICATIONS

Frelin, A.; A New Scintillating Fiber Dosimeter Using a Single Optical Fiber and a CCD Camera; 2006; IEEE Trans. on Nuclear Science; 53(3)1113-1117.
(Continued)

*Primary Examiner* — John Lacyk (57) ABSTRACT

A system for planning radiation treatment therapy is provided. An optical sensor device is implanted within or in close proximity to a risk region within the patient during a radiation delivery. The sensor device optically monitors the orientation of the risk region, and the radiation dosage received by the risk region, during the radiation delivery. That information may be used as appropriate to modify an on-going radiation delivery plan in real time while the plan is being implemented.

23 Claims, 4 Drawing Sheets

(51) Int. Cl.
  *G01T 1/164* (2006.01)
  *A61B 5/06* (2006.01)
  *F21V 8/00* (2006.01)
  *A61B 34/20* (2016.01)

(52) U.S. Cl.
  CPC ......... *A61N 5/1067* (2013.01); *A61N 5/1077* (2013.01); *G01T 1/164* (2013.01); *A61B 2034/2061* (2016.02); *A61N 2005/1051* (2013.01); *A61N 2005/1072* (2013.01); *G02B 6/0003* (2013.01)

(58) Field of Classification Search
  USPC ........................................................ 600/1–8
  See application file for complete search history.

(56) References Cited

U.S. PATENT DOCUMENTS

| | | | |
|---|---|---|---|
| 8,454,648 B1 * | 6/2013 | Isham | A61N 5/1049 128/DIG. 26 |
| 2008/0212082 A1 | 9/2008 | Froggatt et al. | |
| 2009/0236510 A1 | 9/2009 | Lacroix et al. | |
| 2010/0288934 A1 | 11/2010 | Keppel et al. | |
| 2013/0068877 A1 | 3/2013 | Choi et al. | |
| 2013/0131499 A1 | 5/2013 | Chan et al. | |
| 2013/0211261 A1 | 8/2013 | Wang et al. | |
| 2014/0088377 A1 | 3/2014 | Manzke et al. | |

FOREIGN PATENT DOCUMENTS

| | | |
|---|---|---|
| WO | 2012/011914 | 1/2012 |
| WO | 2013068877 A2 | 5/2013 |

OTHER PUBLICATIONS

Hademenos, G. J.; Optimization of a pinhole collimator in a SPECT scintillating fiber detector system: A Monte Carlo analysis; 1994; Radiation Physics and Chemistry; 43(4)383-392.

Hardcastle, N., et al.; In Vivo real-time rectal wall dosimetry for prostate radiotherapy; 2010; Phys. Med. Biol.; 55:3859-3871.

Lacroix, F., et al.; Clinical prototype of a plastic water-equivalent scintillating fiber dosimeter array for QA applications; 2008; Med. Phys.; 35(8)3682-3690.

Nasseri, M. M., et al.; Low energy X-ray imaging using plastic scintillating fiber: A simulation study; 2005; Nuclear Instruments and Methods in Physics Research Section B: Beam Interactions with Materials and Atoms; 234(3)362-368.

Nasseri, M. M., et al.; X-ray imaging using a single plastic scintillating fiber; 2004; Nuclear Instruments and Methods in Physics Research Section B: Beam Interactions with Materials and Atoms; 225(4)617-622.

* cited by examiner

SYSTEM FOR PLANNING RADIATION TREATMENT THERAPY

CROSS REFERENCE TO RELATED APPLICATIONS

This application is a national filing of PCT application Serial No. PCT/IB2013/051535 filed Feb. 26, 2013, published as WO 2013/144736 A1 on Oct. 3, 2013, which claims the benefit of U.S. provisional application Ser. No. 61/615,375 filed Mar. 26, 2012, which is incorporated herein by reference.

The present application relates generally to a method and system for radiation treatment therapy and to the medical imaging arts. Radiation treatment therapy is a process by which trained medical professionals plan and execute a delivery of ionizing radiation to a patient. Very commonly this therapy is used to treat a disease such as cancer by ionizing the diseased tissue, thereby destroying the diseased tissue. In this context, the radiation source is often disposed outside of the person's body to direct the ionizing radiation into the person's body in a controlled manner. Thus, the radiation ionizes both the targeted diseased tissue and the healthy tissue within the path of the radiation. Therefore, a central goal of radiation therapy is to control the radiation delivery to maximize radiation exposure to the targeted diseased regions within the patient's body while minimizing radiation exposure to the at-risk healthy regions within the patient's body.

Radiation therapy typically begins with a diagnostic three-dimensional imaging scan of the patient's body, such as a computed tomography (CT) scan. A trained medical professional uses the diagnostic CT imaging data to specify several characteristics of a radiation therapy delivery plan. For example, using the diagnostic CT imaging data, the medical professional can identify specific target and risk regions within the patient's body. The professional can further specify a minimum radiation dosage to be delivered to the target regions (i.e., enough to destroy the diseased tissue), and a maximum radiation dosage to be delivered to various risk regions (i.e., to limit damage to healthy tissue). Radiation treatment planning software may be used to account for those requirements and other information in designing a set of external radiation source beam delivery angles and shapes that results in the specified radiation dose distributions within the patient's body.

The diagnostic CT scan is performed as close in time as possible to the subsequent radiation treatment delivery. However, it often takes at least several minutes to generate a proposed radiation delivery plan, even using software. Then, the radiation treatment plan as calculated with the software must pass quality assurance tests before the plan is released for delivery to the patient. For these and other reasons, such as patient and doctor scheduling issues, in clinical practice a number of days often passes between the diagnostic CT scan and the radiation treatment delivery.

Once the radiation treatment plan is approved, the radiation is delivered to the patient. The patient is placed within the radiation therapy delivery system in a position which matches, as closely as possible, the patient's position during the prior diagnostic CT imaging scan. However, the position and orientation of the patient's internal organs cannot easily be similarly matched within the small margins which are relevant to radiation treatment therapy. Often, a second diagnostic CT imaging scan is performed just before the radiation is delivered. The results of the second diagnostic scan may be used to reposition the patient before radiation delivery, or as a basis to restart the radiation treatment planning process from the beginning.

Tracking the shape and position of target regions and risk regions within the patient's body during the actual radiation treatment delivery has been traditionally done in clinical practice, if at all, based mostly on external trackers attached to the patient's body. Such external tracking allows only indirect conclusions to be reached regarding the shape and position of target regions and risk regions within the patient's body.

It has however been proposed to use a radiation dosimeter in combination with Fiber Optic Shape Sensing and Localization (FOSSL) tracking technology to measure the radiation dose applied to target regions during radiation treatment delivery. See U.S. Provisional Patent Application Ser. No. 61/556,315, to inventors M. Grass, R. Manzke, and R. Chan, entitled "Flexible X-Ray Detector with Optical Shape Sensing", filed on Nov. 7, 2011 (hereafter "Grass et al."). The present application hereby incorporates Grass et al. herein by reference for its disclosure concerning combined radiation dosimeter and fiber optic tracking sensor devices and methodologies.

A radiation dosimeter is a device that measures the amount of ionizing radiation present in the area where the dosimeter is located, or some other related quantity which is indicative of such radiation. Radiation dosimeters can be manufactured to be very small in size, such as a few millimeters in diameter, but still provide a high degree of measurement accuracy.

FOSSL technology, by contrast, tracks the orientation of an optical wire. The "orientation" of an optical wire as specially defined herein corresponds to identifying a shape and a position of the optical wire relative to a designated reference point. This is accomplished for example via a plurality of sensors placed along the length of the optical fiber to measure deflections and bending of the optical fiber. Such FOSSL tracking technology is generally described, for example, in the following three patent applications:

WO 2011/098926, to inventors R. Chan, G. Shechter, A. E. Desjardins, G. 'T Hooft, and C. S. Hall, entitled "Apparatus, System and Method for Imaging and Treatment Using Optical Position Sensing", filed on Jan. 14, 2011 and designating the United States, claiming priority to U.S. Provisional Patent Application Ser. No. 61/302,571, filed on Feb. 9, 2010;

WO 2011/138691, to inventors J. Wang, R. Chan, G. 'T Hooft, A. E. Desjardins, and C. S. Hall, entitled "Motion Compensation and Patient Feedback in Medical Imaging Systems", filed on Mar. 29, 2011 and designating the United States, claiming priority to U.S. Provisional Patent Application Ser. No. 61/332,212, filed on May 7, 2010; and U.S. Provisional Patent Application Ser. No. 61/514,585, to inventors R. Manzke, G. 'T Hooft, R. Chan, and A. E. Desjardins, entitled "Dynamic Constraining with Optical Shape Sensing", filed on Aug. 3, 2011.

The present application incorporates those three prior applications herein by reference for their respective disclosures of FOSSL tracking technologies and methods.

As already stated, Grass et al. propose using a radiation dosimeter in combination with fiber optic tracking technology to measure the radiation dose applied to target regions during radiation treatment delivery. The Grass et al. sensor device is placed within or in close proximity to the target region, and measures both the radiation dosage being applied to the target region and the orientation of the target region over time during radiation delivery. In this way, a radiation therapy treatment can be applied to the target region and dynamically adjusted during radiation delivery to account for movement or shape shifting of the target region.

The present disclosure concerns a further use of the Grass et al. sensor device and related methodologies, and also a specific case example for using this technology. In the first aspect, a radiation dosimeter in combination with fiber optic tracking technology is used to monitor risk regions (not only target regions) during radiation treatment delivery.

In the second aspect, a radiation dosimeter in combination with fiber optic tracking technology is used to treat prostate cancer with radiation therapy. In this context, the at risk regions include portions of the rectal wall which are disposed near to the prostate tissue. Therefore, a rectal balloon may be used both to stabilize the shape and position of the rectum during radiation delivery, as well as to monitor that orientation and the amount of radiation being delivered to the rectum wall. Changes to the radiation delivery plan, potentially including a full stoppage of radiation delivery and/or a modification of the plan, may be implemented in real time during radiation delivery based on the monitored information.

Using the present invention, outcomes for radiation treatment therapy will improve by considering morphological changes of risk regions within the patient during radiation delivery. Risk regions are more effectively preserved and target regions receive their prescribed radiation dose more reliably. Online monitoring of radiation dose at risk regions increases patient safety. It also enables advanced treatment regimes such as refocusing or otherwise adjusting the radiation beam based on the orientation tracker signal during the radiation delivery. For example, one major structure at risk in prostate treatment is the rectal wall.

The method comprises implanting an optical sensor device into the patient, within or in close proximity to at least one risk region within the patient. The optical sensor device has an orientation fiber core configured to measure an orientation of the optical sensor device relative to a point of reference, and a radiation fiber core configured to measure a dose of radiation received by the optical sensor device. Both fiber cores are optically interrogated during radiation delivery to generate orientation information and radiation dosage information regarding the optical sensor device. That information is used to estimate an orientation of the optical sensor device, and a radiation dosage received by the optical sensor device, during radiation delivery. Those estimates are then monitored during the radiation delivery, and may be used as appropriate to modify an on-going radiation delivery plan in real time while the plan is being implemented. Corresponding optical sensing systems and radiation delivery planning systems are also provided.

Numerous advantages and benefits will become apparent to those of ordinary skill in the art upon reading the following detailed description of several embodiments. The invention may take form in various components and arrangements of components, and in various process operations and arrangements of process operations. The drawings are only for the purpose of illustrating many embodiments and are not to be construed as limiting the invention.

The present disclosure describes methods and systems for using a radiation dosimeter in combination with an optical shape and position tracking system. The methods and systems may be used in conjunction with a radiation therapy delivery system. They may further be used in conjunction with any one or more of various imaging system modalities, including for example x-ray based imaging, ultrasound imaging, computed tomography (CT) imaging, magnetic resonance imaging (MRI), and the like.

Figure 1:
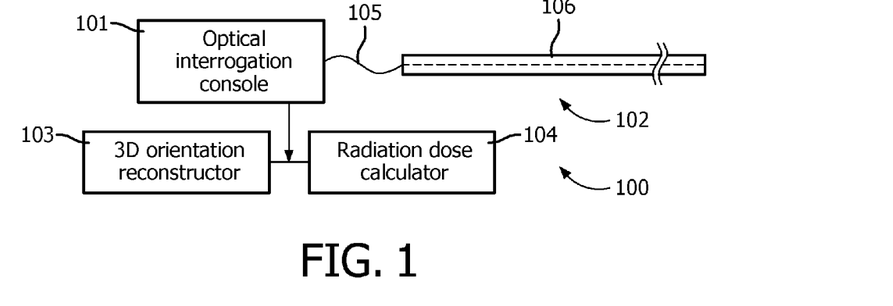
FIG. 1 schematically illustrates an optical sensing system 100, which monitors a radiation dose received by and an orientation of an optical sensor device.

FIG. 1 schematically illustrates an optical sensing system 100. The optical sensing system 100 has an optical interrogation console 101 optically connected to at least one optical sensor device 102 and electronically connected to a three-dimensional orientation reconstructor 103 and a radiation dose calculator 104. The optical interrogation console 101 sends an optical interrogation signal to an optical wire 105 which is embedded within or on a substrate material 106 to form the optical sensor device 102. The optical signal travels out to the optical sensor device 102 and is then reflected back through the wire 105, in a manner described further below, to the console 101. The reflected optical signal carries information which is indicative of some property of the optical sensor device 102. That information includes either an orientation of the optical sensor device 102, or an amount of radiation received by the optical sensor device 102, or both those properties. The optical interrogation console 101 measures the reflected light, and electronically passes the measurements on to the three-dimensional orientation reconstructor 103 and/or the radiation dose calculator 104 for analysis.

Figure 2:
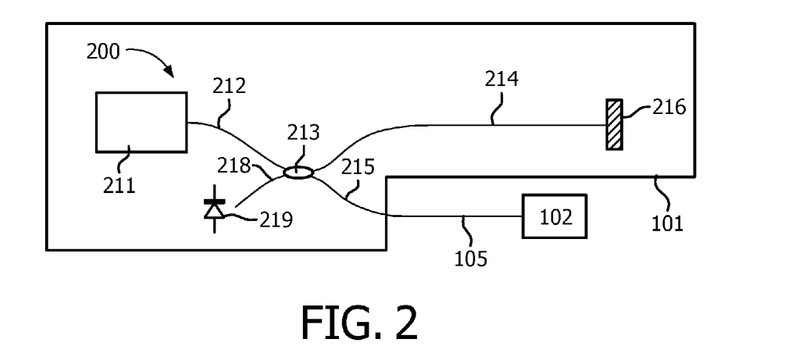
FIG. 2 schematically illustrates an optical Fourier domain reflectometer system 200 which may be used in conjunction with the optical sensing system 100.

The optical interrogation console 101 may be any device or system structurally configured for transmitting light to the optical wire 105 and receiving and measuring reflected light back from the optical wire 105. In one embodiment, the optical interrogation console 101 employs at least one optical Fourier frequency domain reflectometer and other appropriate electronics or devices as known in the art. The principles of such a reflectometer 200 are illustrated in FIG. 2. Other suitable optical interrogation console 101 setups are known and can be used in the optical sensing system 100.

The reflectometer system 200 has a tunable light source 211 with a coherent light output 212 which may be tuned to have a desired wavelength. The light output 212 of the light source 211 travels through a splitter 213 which splits the light signal 212 into a reference channel 214 and a sample channel 215. The light which enters the reference channel 214 travels to a mirror 216 to reflect back to the splitter 213 along the reference channel 214, which has a known and constant optical path length. The light which enters the sample channel 215 travels to the external optical wire 105, where it interacts with the optical sensor device 102 and is reflected back to the splitter 213 along the same path 105 and 215. The combined optical path length of the sample channel 215 and the external optical wire 105 is a known constant.

The two optical signals reflected back to the splitter 213 are then combined into a measurement optical signal 218 by the splitter 213 and directed to a photo detector 219. The photo detector 219 records the measurement optical signal 218. By varying the light output 212 properties in a known and controlled manner, and recording the resulting measurement optical signals 218 as the light output 212 is varied, the reflectometer system 200 creates an interference pattern. The interference pattern is indicative of either an orientation of the optical sensor device 102, or an amount of radiation received by the optical sensor device 102, or both. The optical interrogation console 101 measures the interference pattern, and electronically sends the recorded information to the three-dimensional orientation reconstructor 103 and/or the radiation dosimeter calculator 104 for analysis.

Referring again to FIG. 1, the optical wire 105 may be any type of flexible material suitable for carrying the light signals to and from the optical sensor device 102. Suitable materials include, for example, flexible and optically transparent glass or plastic materials. Other suitable materials may be used. The optical wire 105 may contain a single optical fiber core, or multiple optical fiber cores.

The substrate 106 may be any type of material suitable for embedding, carrying or otherwise supporting the optical wire 105. Suitable examples of appropriate substrates 106 include, but are not limited to, deployable balloons such as rectal balloons, catheters, filters, baskets, helixes, endoscopes, and the like. The substrate 106 and/or the optical wire 105 supported by the substrate 106 may form a shape comprising one or more of an elongated straight shape, a curved line shape, a spiral shape, a ring shape, a loop shape, a helix shape, or any other shape. The material and shape of the substrate 106 may be changed to provide different results depending on the clinical application, for example by better fitting to a specific organ or tumor. The specific substrate 106 may also be selected based on the type of tissue present where the optical sensor device 102 is to be inserted into a patient. In this way the optical wire 105 and the substrate 106 together form a flexible and configurable volume to obtain orientation information and radiation dose information from the optical sensor device 102. However, in some embodiments, the optical sensor device 102 may comprise solely an optical wire 105, without any substrate 106.

The optical wire 105 can be used to obtain orientation information regarding the optical sensor device 102 using fiber optic tracking technology, as discussed above. This is done by optically interrogating one or more orientation fiber cores within the optical wire 105. In a first embodiment, for example, the orientation fiber core(s) each incorporate an array of Bragg gratings integrated along a length of the optical wire 105 as known in the art. In a second embodiment, as another example, the orientation fiber core(s) each have natural variations in optic refractive index occurring along the length of the wire as known in the art, such as a Rayleigh scattering based optical fiber core. Other fiber optic orientation tracking devices or structures may alternatively or additionally be used.

The interference patterns created by the light reflected from such structures in the orientation fiber core(s) of the optical wire 105 are recorded by the optical interrogation console 101 and passed on to the three-dimensional orientation reconstructor 103. The three-dimensional orientation reconstructor 103 is broadly defined herein as any device or system structurally configured for translating measured reflection spectra data received from the orientation fiber core(s) of the optical wire 105 into a three-dimensional orientation of the optical sensor device 102. For example, an axial reflectivity profile (A-line) of the optical sensor device 102 may be obtained by discrete Fourier transform (DFT) of the sampled signals. Also, in some embodiments, the sampled signals may be combined with one or more biophysical models to derive the estimated orientation information.

The optical wire 105 can also be used to obtain radiation dosage information regarding radiation received at the optical sensor device 102 using fiber optic technology. This is done by optically interrogating one or more radiation fiber cores within the optical wire 105. In a first embodiment, for example, the radiation fiber core(s) may have the cladding structure shown in FIG. 3. In another embodiment (not illustrated), the radiation fiber core(s) are disposed next to one or more scintillators which are affixed to the optical wire such as with an optically transparent adhesive. Other fiber optic radiation dosimeters may alternatively or additionally be employed in the optical sensor device 102.

Figure 3:
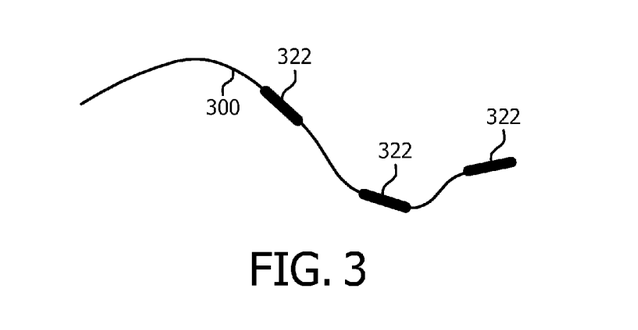
FIG. 3 schematically illustrates an optical wire fiber core 300 incorporating a number of different scintillating claddings for on-line radiation dose measurements during radiation delivery.

The exemplary radiation fiber core 300 of FIG. 3 is a flexible optical fiber having a cross-section which is comparatively small relative to the length of the core 300. The radiation fiber core 300 includes one or more cladding areas 322 along its length. The radiation fiber core 300 may comprise multiple areas of cladding 322 distributed along a length of the optical sensor device 102, to achieve a higher resolution of radiation dosage measurement. Three cladding areas 322 are illustrated in FIG. 3, but in other embodiments more or less cladding areas 322 may be provided. The cladding(s) 322 convert incoming radiation into visible light, which will interact with the interrogation light 212 passing through the radiation fiber core 300 from the optical interrogation console 101. The cladding(s) 322 may be a scintillating cladding material. The cladding(s) 322 may be optimized for different energies of the incoming radiation, such as for example diagnostic X-ray energies or photon energies used in radiation therapy. The cladding(s) 322 may only be partial claddings or they may be radiation shielded, in order to derive additional directional information regarding the radiation which reaches the optical sensor device 102.

The interference patterns created by light reflected from such structures in the radiation fiber core(s) of the optical wire 105 are recorded by the optical interrogation console 101 and passed on to the radiation dose calculator 104. The radiation dose calculator 104 is broadly defined herein as any device or system structurally configured for translating measured reflection spectra data received from the radiation fiber core(s) of the optical wire 105 into a measurement of the radiation dosage received at the optical sensor device 102. In some embodiments, the sampled signals may be combined with one or more radiation dosage models to derive the estimated radiation information.

The optical orientation interrogation components and the optical radiation interrogation components within the system 100 may be entirely separate from each other. That is, the optical sensing system 100 may include a first, orientation reflectometer 200 dedicated to the orientation fiber core(s) within the optical wire 105 for the sole use of obtaining orientation information concerning the optical sensor device 102. That system 100 would then include a second, radiation dosage reflectometer 200 dedicated to the radiation fiber core(s) within the optical wire 105 for the sole use of obtaining radiation dosage information concerning the optical sensor device 102.

In other embodiments, however, the orientation and radiation optical subsystems within the optical sensing system 100 may share one or more components. Thus, a single reflectometer 200 may be used to optically interrogate separate orientation and radiation fiber cores in order to monitor the optical sensor device 102. Or, a single fiber may be used as both an orientation fiber and as a radiation fiber. In such embodiments, it may be useful for the two subsystems to use different wavelengths of optical interrogation light in order to differentiate between the two optical signals, as known in the art.

The three-dimensional orientation reconstructor 103 and the radiation dose calculator 104 both include a processor and a memory for performing suitable calculations. While FIG. 1 illustrates the orientation reconstructor 103 and the dosimeter calculator 104 as separate components, they may in some embodiments comprise a single processor, with a common memory. Thus the functions described herein can be performed as software logic. "Logic," as used herein, includes but is not limited to hardware, firmware, software and/or combinations of each to perform a function(s) or an action(s), and/or to cause a function or action from another component. For example, based on a desired application or needs, logic may include a software controlled microprocessor, discrete logic such as an application specific integrated circuit (ASIC), or other programmed logic device. Logic may also be fully embodied as software.

"Software," as used herein, includes but is not limited to one or more computer readable and/or executable instructions that cause a computer or other electronic device to perform functions, actions, and/or behave in a desired manner. The instructions may be embodied in various forms such as routines, algorithms, modules or programs including separate applications or code from dynamically linked libraries. Software may also be implemented in various forms such as a stand-alone program, a function call, a servlet, an applet, instructions stored in a memory, part of an operating system or other type of executable instructions. It will be appreciated by one of ordinary skill in the art that the form of software is dependent on, for example, requirements of a desired application, the environment it runs on, and/or the desires of a designer/programmer or the like. The Logic of the orientation reconstructor 103 and the radiation dose calculator 104 may most easily be embodied as part of a radiation therapy planning software package.

The methods and systems described herein can be implemented on a variety of platforms including, for example, networked control systems and stand-alone control systems. Additionally, the logic shown and described herein preferably resides in or on a computer readable medium. Examples of different computer readable media include Flash Memory, Read-Only Memory (ROM), Random-Access Memory (RAM), programmable read-only memory (PROM), electrically programmable read-only memory (EPROM), electrically erasable programmable read-only memory (EEPROM), magnetic disk or tape, optically readable mediums including CD-ROM and DVD-ROM, and others. Still further, the processes and logic described herein can be merged into one large process flow or divided into many sub-process flows. The order in which the process flows herein have been described is not critical and can be rearranged while still accomplishing the same results. Indeed, the process flows described herein may be rearranged, consolidated, and/or re-organized in their implementation as warranted or desired.

Figure 4:
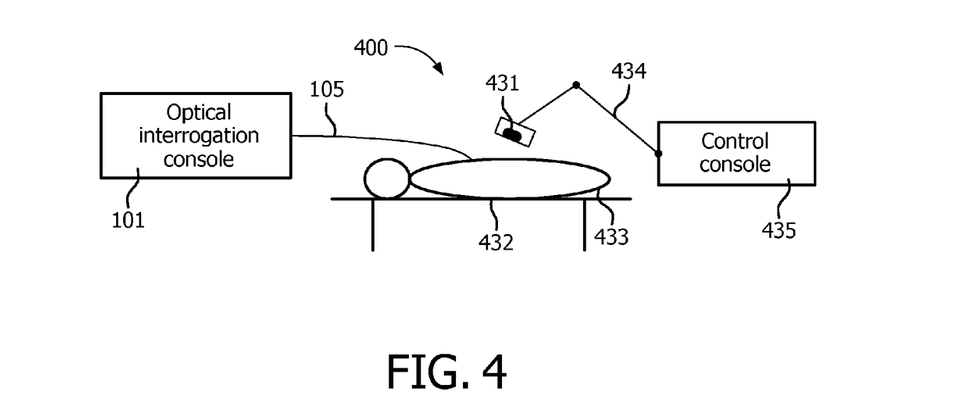
FIG. 4 schematically illustrates a radiation therapy system 400 incorporating the optical sensing system 100 of FIG. 1.

FIG. 4 schematically illustrates a radiation therapy system 400 including a movable radiation source 431 for directing and providing radiation to a designated target region 432 within a patient 433. The radiation source 431 may be, for example, an x-ray source or some other suitable source for providing radiation for radiation therapy. The radiation source 431 may be mounted on a movable arm 434 thereby providing a movable radiation source 431 for directing and providing radiation to the designated target region 432. The target region 432 may be, for example, a tumor in the patient 433.

The radiation therapy system 400 further includes the optical sensing system 100 described above. Thus, one end of the optical wire 105 is connected to the optical interrogation console 101, and the other, distal end incorporates the optical sensor device 102. The distal end of the optical wire 105 and the optical sensing device 102 are inserted into the patient 433 during a radiation therapy delivery or other procedure to monitor the orientation of and the radiation dose received by risk regions and perhaps also target regions within the patient 433.

The radiation therapy system 400 additionally includes a control console 435 which has one or more processors (not shown) to move and operate the radiation source 431. The processors of the control console 435 may contain Software Logic, as defined above, to perform those and other functions. The respective functions of the three-dimensional shape reconstructor 103, the radiation dose calculator 104, and the system control console 435 may be performed by one single processor or multiple processors working together.

Figure 5:
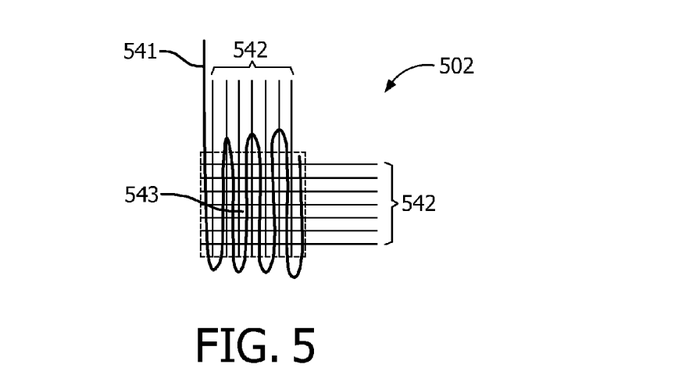
FIG. 5 schematically illustrates an optical sensor device 502 having a configurable volume.

FIG. 5 illustrates one exemplary form of an optical sensor device 502 having a configurable volume which may be used in connection with the optical sensing system 100. The device 502 comprises one orientation fiber core 541 interweaved with two radiation fiber cores 542 in order to form a flexible two-dimensional mesh sensing array 543. An appropriate substrate (not shown) may be added to the device 502 in order to hold the cores 541 and 542 together in the flexible mesh shape 543. The flexible mesh 543 forms a contour conforming sensor array which can be wrapped around the exterior contours of a risk region in order to monitor the orientation of and the radiation dose applied to the risk region.

Figure 6A:
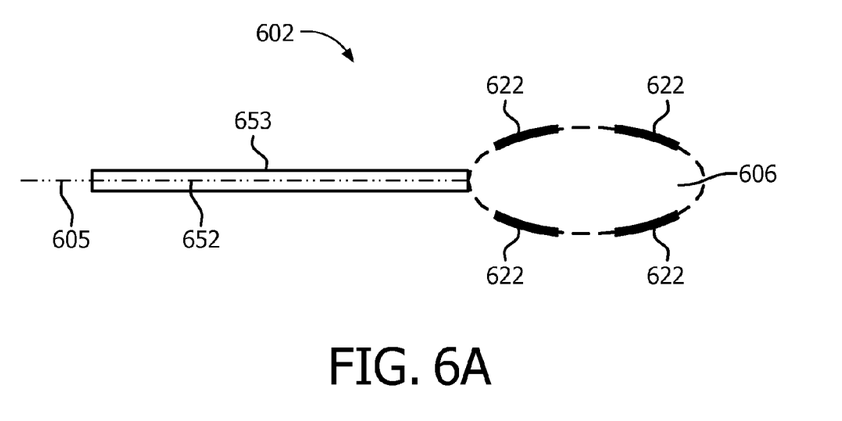
FIG. 6A schematically illustrates an optical sensor device 602, having a configurable volume in a relaxed state.

FIG. 6A illustrates a second exemplary form of an optical sensor device 602 having a configurable volume which may be used in connection with the optical sensing system 100. The device 602 comprises an optical wire 605 having at least one orientation fiber core (not shown) and at least one radiation fiber core 652. The optical wire 605 extends through a substrate wire guide 653 to a balloon substrate 606, such as a rectal balloon as is commonly used during prostate cancer radiation treatment. The balloon 606 is shown in a relaxed state in FIG. 6A. The size of the balloon 606 as illustrated is somewhat exaggerated. In actual use, an uninflated balloon 606 would more typically cling tightly to the optical wire without much room for movement. The orientation fiber core(s) and the radiation fiber core(s) 652 are mounted in or on the surface of the balloon 606 substrate. The specific radiation fiber core 652 illustrated in FIG. 6A contains four radiation dose sensor structures 622, such as cladding structures, which are disposed around the periphery of the balloon 606. The fiber cores of the optical wire 605 may be disposed on the balloon 606 in a crossing sensor array to increase the sensitivity of the measurements and to stabilize the array.

Figure 6B:
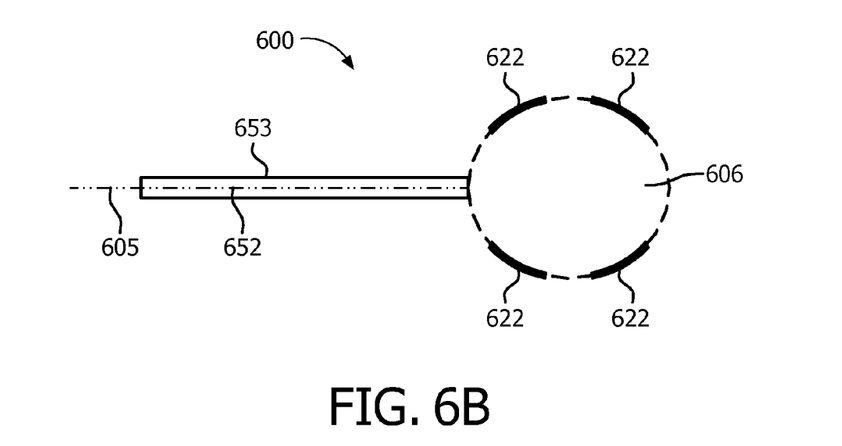
FIG. 6B schematically illustrates the device 602 of FIG. 6A, with the configurable volume in an inflated state.

FIG. 6B schematically illustrates the optical sensor device 602 with the balloon 606 in an inflated state. The balloon 606 may be inflated with an inert gas or the like, as known in the catheter balloon art. In this way, the optical sensor device 602 forms a contour conforming sensor array which can be inflated to conform to the interior contours of a risk region in order to monitor the orientation of and the radiation dose applied to the risk region. In some embodiments, the balloon 606 may be inflated with a radiation absorbing liquid instead of an inert gas, in order to further reduce radiation delivered to risk regions.

Figure 7:
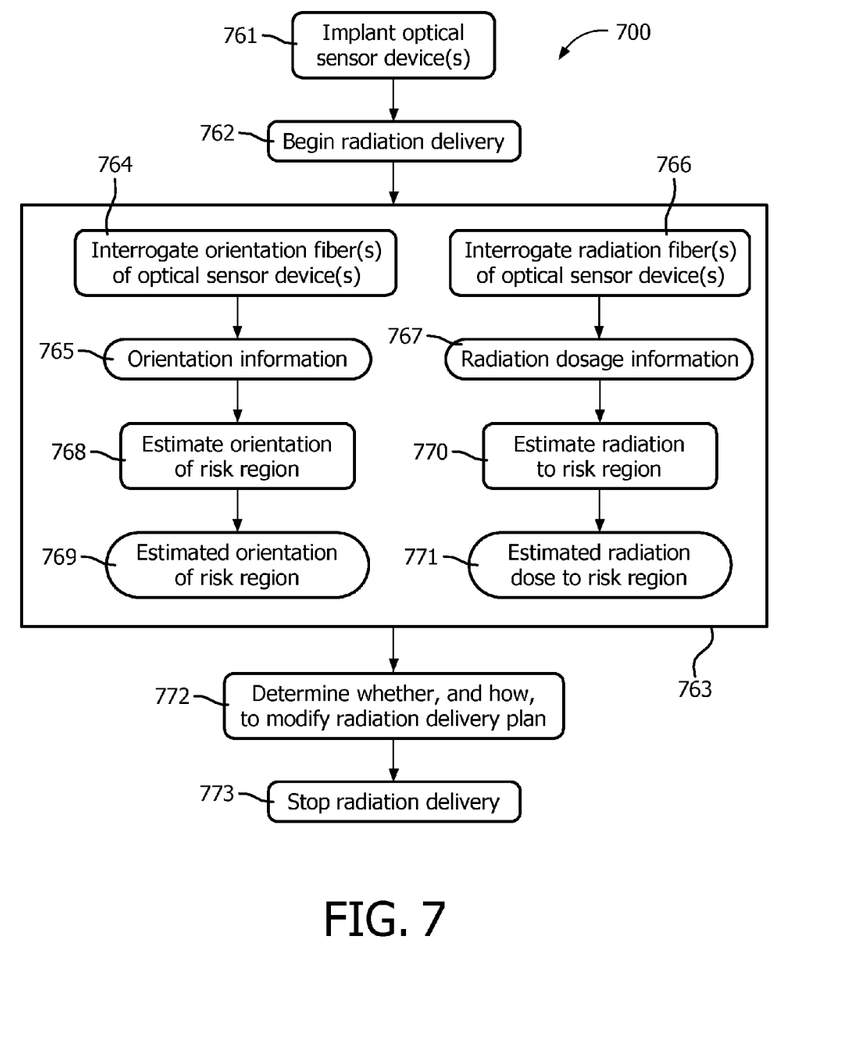
FIG. 7 schematically illustrates steps of a method for using an optical sensing system during a radiation therapy treatment.

Thus a method for using the optical sensing system 100 during a radiation therapy treatment is provided. An exemplary such method 700 is illustrated in FIG. 7. In a first step 761, an optical sensor device 102 is implanted into a patient either within or in close proximity to at least one risk region to be treated with radiation. Other optical sensor devices 102 may also be embedded within or in close proximity to additional risk regions, or one or more target regions, within the patient's body. The patient is placed within a radiation therapy system, such as the exemplary system 400 discussed above. The radiation therapy system then begins 762 to deliver radiation to the patient.

During the radiation delivery procedure, the optical sensing system 100 is utilized to monitor 763 the orientation of the risk region within the patient, and an amount of radiation received by the risk region. More specifically, the orientation fiber(s) in the optical wire 105 are interrogated 764 by the optical interrogation console 101 to obtain risk region orientation information 765 during radiation delivery. The risk region orientation information 765 comprises measuring the light signals returning from the optical sensor device 102 as a function of the interrogation light properties. If the optical wire 105 contains multiple orientation fiber cores, this information 765 may be recorded separately for each core. The light reflection within the optical sensor device 102 may be invoked for example by embedded periodical structures within the optical wire 105 (e.g., Fiber Bragg Gratings) or by non-periodic, random variations in the refractive index of the optical wire 105 (e.g., Rayleigh scattering).

The radiation fiber(s) in the optical wire 105 are similarly interrogated 766 to obtain radiation dosage information 767 during radiation delivery. These respective interrogations 764 and 766 may be performed simultaneously, or sequentially, and in any number or order with respect to each other, as appropriate to obtain sufficient measurement information 765 and 767 regarding the risk region. Further, if more than one risk region, or a target region, is also monitored then similar interrogations are made of the optical sensor devices disposed in those regions.

The orientation information 765 is provided to the three-dimensional orientation reconstructor 103, which uses the orientation information to estimate 768 an orientation 769 of the risk region within the patient's body. The three-dimensional shape reconstructor 103 may, for example, process the reflection spectra 765 to generate strain values at multiple positions along the orientation fiber core(s) of the optical wire 105. The strain sensors may comprise at least one of a Fiber Bragg Grating (FBG) and a Rayleigh scatter interrogation.

The optical wire 105 may in some embodiments advantageously include an area of higher sensitivity by including an area with a higher number of optical fibers having optical strain sensors. For example, the optical wire 105 may have a first area where a first number of optical fibers having optical strain sensors are present, and a second area where a second number of optical fibers having optical strain sensors are present. In this way the second area will have a higher sensitivity than the first area. The higher sensitivity may help achieve a better resolution regarding the orientation of the optical wire 105. As one example, the first area may have one optical fiber and a first sensitivity, and the second area may have four optical fibers and a second sensitivity which is higher than the first sensitivity. The three-dimensional shape reconstructor 103 combines the strain values to generate a three-dimensional reconstruction of the shape and position of the optical wire 105. For example, the strain measurements may be converted to rotation angles and the associated rotation matrices may be used to update a tangent vector, a normal vector and a binormal vector (i.e. columns of a Jacobian matrix).

The radiation dosage information 767 is similarly provided to the radiation dose calculator 104, which uses the radiation information to estimate 770 a dose of radiation 771 received by the risk region within the patient. Similar radiation dosage calculations are made with respect to other monitored risk regions, or target regions.

The risk region orientation and radiation dose estimates 769 and 771 are provided to a radiation therapy planning system processor during radiation delivery. The radiation therapy planning system registers the coordinate systems of the estimates 769 and 771 with the coordinate system of the radiation delivery system. It then uses the estimated information to determine 772 whether, and if so how, to modify the radiation delivery plan in response to movement of the patient during radiation delivery. Such movement may comprise, for example, breathing motion, cardiac motion, peristaltic motion, or other patient-induced movements. The radiation delivery plan modifications may include, for example, stopping the radiation delivery if the risk region has received a pre-set maximum radiation dose. In other cases, where the risk region has undergone a significant change in orientation during the radiation delivery, the radiation delivery may be continued but the plan modified to account for the morphological changes in order to protect the risk region.

In yet additional embodiments, the radiation therapy planning system may use the risk region orientation and radiation dose estimates to provide a notification to a user of the system concerning the estimates. The user notification may take many forms. In one embodiment, the system may simply notify the user that the radiation dose received by the risk region has achieved a stated percentage of a pre-set maximum value. In another embodiment, the system may additionally present the user with a proposed modification of the radiation delivery plan in order to account for changes in risk region orientation during radiation delivery.

Eventually, the radiation delivery plan will run its course. The plan may have been modified 772 as a result of the monitoring 763, or not. Either way, the radiation delivery is stopped 773 when the plan has run its course. In some situations the radiation delivery may be fractionated, that is, distributed among multiple delivery sessions rather than a single delivery session. In that event, the estimates 769 and 771 from earlier delivery sessions may be used in the planning and modification of subsequent delivery sessions.

In one exemplary embodiment, the optical sensing system 100 is used during radiation treatment therapy to treat prostate cancer. In this context, the target region is cancerous tissue within the patient's prostate gland or surrounding tissue. Risk regions include portions of the rectal wall which are disposed near the prostate gland, and the patient's bladder. For example, severe side effects including rectal cancer have been observed due to radiation dose that was erroneously directed to healthy rectal tissue rather than cancerous prostate tissue during prostate cancer radiation treatment. Similar risks are also presented to nearby bladder tissue.

To reduce such side effects, standard protocols have been developed to protect rectal tissue and bladder tissue from over-exposure to radiation during prostate cancer radiation treatment. As to rectal tissue, it is customary to deploy one or more balloons within the patient's rectum to stabilize the size and position of the patient's rectal tissue during prostate radiation treatment delivery. As to bladder tissue, it is customary to mandate a controlled bladder filling state during prostate radiation treatment delivery, for example by asking the patient to drink a bottle of water a suitable time before the radiation delivery. However, even taking such precautions, the size and relative positions of the patient's rectum, bladder and prostate may not be well controlled within the small margins relevant for radiation therapy. This is especially true for position changes due to respiratory motion, but also for physiological effects like rectal gas and its movement. Thus, online tracking of actual delivered radiation dosage and comparison with the planned risk region dosage is highly beneficial to optimize the treatment.

To use the optical sensing system 100 in conjunction with prostate cancer treatment, a first optical sensor device 102 may be incorporated into a rectal balloon. A representative example 602 of such a device is illustrated in FIGS. 6A and 6B. This first optical sensor device can be interrogated to monitor the orientation of and radiation dose received by the rectum risk region during prostate radiation treatment delivery. The balloon may advantageously be filled with a radiation absorbing fluid such as a liquid metal to reduce the radiation which reaches the back side of the rectal wall, furthest away from the prostate tissue.

In addition, a second optical sensor device may also be placed in close proximity to the bladder. A representative example 502 of such a device is illustrated in FIG. 5. This second optical sensor device can be interrogated to monitor the orientation of and radiation dose received by the bladder risk region during prostate radiation treatment delivery.

The invention has been described with reference to the several embodiments. Obviously, modifications and alterations will occur to others upon reading and understanding the preceding detailed description. For example, the optical sensing system 100 may be used in conjunction with nuclear medicine guided interventions. It is intended that the invention be construed as including all such modifications and alterations insofar as they come within the scope of the appended claims or the equivalents thereof. The invention may take form in various compositions, components and arrangements, combinations and sub-combinations of the elements of the disclosed embodiments.

Having thus described several embodiments, the invention is now claimed to be:

1. A method of operating a radiation delivery system according to a radiation delivery plan, wherein the radiation delivery system comprises a movable radiation source for directing and providing radiation to a designated target region within a patient, the method comprising:
    implanting an optical sensor device into the patient, within or in close proximity to at least one risk region within the patient, wherein a risk region comprises tissue not targeted by the radiation delivery plan, the optical sensor device comprising at least one orientation fiber core configured to measure an orientation of the optical sensor device relative to a point of reference, and at least one radiation fiber core configured to measure a dose of radiation received by the optical sensor device;
    optically interrogating the at least one orientation fiber core to generate orientation information regarding the optical sensor device during a radiation delivery to the patient, and using the orientation information to estimate a risk region orientation during the radiation delivery;
    optically interrogating the at least one radiation fiber core to generate radiation dosage information regarding the optical sensor device during the radiation delivery, and using the radiation dosage information to estimate a risk region radiation dosage during the radiation delivery; and
    determining whether to modify the radiation delivery plan based on at least one of the estimated risk region orientation and the estimated risk region radiation dosage during the radiation delivery.

2. The method of claim 1, further comprising modifying an initial radiation delivery plan to form an updated radiation delivery plan based on at least one of the estimated risk region orientation and the estimated risk region radiation dosage.

3. The method of claim 1, wherein the patient is being treated for prostate cancer, the at least one risk region comprises rectal tissue, and the optical sensor device comprises a rectal balloon which is implanted within the patient's rectum during the radiation delivery.

4. A radiation therapy planning system for use in generating a radiation delivery plan to be implemented by a radiation delivery system comprising a movable radiation source for directing and providing radiation to a designated target region within a patient, the planning system comprising:
    an optical sensor device for being implanted within or in close proximity to at least one risk region within the patient, wherein a risk region comprises tissue not targeted by the radiation delivery plan, and comprising at least one orientation fiber core configured to measure an orientation of the optical sensor device relative to a point of reference, and at least one radiation fiber core configured to measure a dose of radiation received by the optical sensor device;
    an optical interrogation console for optically interrogating the at least one orientation fiber core to generate orientation information regarding the optical sensor device during a radiation delivery to the patient, and optically interrogating the at least one radiation fiber core to generate radiation dosage information regarding the optical sensor device during the radiation delivery;
    an orientation reconstructor to estimate a risk region orientation based on the orientation information during the radiation delivery;
    a radiation dosage calculator to estimate a risk region radiation dosage based on the radiation information during the radiation delivery; and
    a processor for determining whether to modify the radiation delivery plan based on at least one of the estimated risk region orientation and the estimated risk region radiation dosage during the radiation delivery.

5. The system of claim 4, wherein the optical interrogation console comprises a single reflectometer to optically interrogate the at least one orientation fiber core and to optically interrogate the at least one radiation fiber core.

6. The system of claim 4, wherein the optical sensor device comprises a substrate supporting the at least one orientation fiber core and the at least one radiation fiber core.

7. The system of claim 6, wherein the substrate comprises a balloon.

8. The system of claim 6, wherein the optical sensor device comprises a configurable volume.

9. The system of claim 4, wherein the radiation fiber core comprises at least one cladding for converting incoming radiation into visible light.

10. The system of claim 4, wherein the optical sensor device comprises an intraluminal flexible body having a cross-section being comparatively small relative to a length of the device, and the orientation fiber core is configured to collect information regarding an orientation of the intraluminal structure.

11. The system of claim 4, wherein the processor is configured to modify an initial radiation delivery plan to form an updated radiation delivery plan based on at least one of the estimated risk region orientation and the estimated risk region radiation dosage.

12. The system of claim 4, wherein the optical sensor device further comprises a rectal balloon for insertion into the patient's rectum during the radiation delivery.

13. The system of claim 4, wherein the orientation reconstructor uses the orientation information to generate local strain data for a plurality of positions along the at least one orientation fiber core, and to generate local curvature and torsion angle data as a function of each local strain along the orientation fiber core, and to reconstruct the three-dimensional shape of the orientation fiber core as a function of each local curvature and torsion angle.

14. An optical sensing system comprising:
   an optical sensor device for being implanted within or in close proximity to at least one risk region within a patient, wherein a risk region comprises tissue not targeted by a radiation delivery plan, and comprising at least one orientation fiber core configured to measure an orientation of the optical sensor device relative to a point of reference, and at least one radiation fiber core configured to measure a dose of radiation received by the optical sensor device;
   an optical interrogation console for optically interrogating the at least one orientation fiber core to generate orientation information regarding the optical sensor device during a radiation delivery to the patient, and optically interrogating the at least one radiation fiber core to generate radiation dosage information regarding the optical sensor device during the radiation delivery;
   an orientation reconstructor to estimate a risk region orientation based on the orientation information during the radiation delivery;
   a radiation dosage calculator to estimate a risk region radiation dosage based on the radiation information during the radiation delivery; and
   a processor for monitoring the estimated risk region orientation and the estimated risk region radiation dosage during the radiation delivery.

15. The method of claim 1, wherein determining whether to modify the radiation delivery plan comprises comparing the estimated risk region radiation dosage to a predetermined maximum value.

16. The method of claim 1, further comprising modifying the radiation delivery based on at least one of the estimated risk region orientation and the estimated risk region radiation dosage during the radiation delivery.

17. The method of claim 1, further comprising stopping the radiation delivery based on at least one of the estimated risk region orientation and the estimated risk region radiation dosage during the radiation delivery.

18. The method of claim 1, further comprising:
   implanting a second optical sensor device into the patient, within or in close proximity to at least one target region within the patient, wherein the target region comprises tissue targeted by the radiation delivery plan, the second optical sensor device comprising at least one orientation fiber core configured to measure an orientation of the second optical sensor device relative to a point of reference, and at least one radiation fiber core configured to measure a dose of radiation received by the second optical sensor device;
   optically interrogating the at least one orientation fiber core to generate orientation information regarding the second optical sensor device during the radiation delivery to the patient, and using the orientation information to estimate a target region orientation during the radiation delivery;
   optically interrogating the at least one radiation fiber core to generate radiation dosage information regarding the second optical sensor device during the radiation delivery, and using the radiation dosage information to estimate a target region radiation dosage during the radiation delivery; and
   determining whether to modify the radiation delivery plan further based on at least one of the estimated target region orientation during the radiation delivery and the estimated target region radiation dosage during the radiation delivery.

19. The method of claim 18, further comprising modifying the radiation delivery plan based on the estimated risk region radiation dosage during the radiation delivery and the estimated target region radiation dosage during the radiation delivery.

20. The system of claim 4, further comprising:
   a second optical sensor device for being implanted within or in close proximity to at least one target region within the patient, wherein the target region comprises tissue targeted by the radiation delivery plan, and comprising at least one orientation fiber core configured to measure an orientation of the second optical sensor device relative to a point of reference, and at least one radiation fiber core configured to measure a dose of radiation received by the second optical sensor device;
   wherein the system optically interrogates the at least one orientation fiber core to generate orientation information regarding the second optical sensor device during the radiation delivery to the patient and optically interrogates the at least one radiation fiber core to generate radiation dosage information regarding the second optical sensor device during the radiation delivery, to estimate a target region orientation during the radiation delivery and estimate a target region radiation dosage during the radiation delivery; and
   wherein the processor determines whether to modify the radiation delivery plan further based on at least one of the estimated target region orientation during the radiation delivery and the estimated target region radiation dosage during the radiation delivery.

21. The system of claim 4, wherein a single fiber comprises the at least one orientation fiber core and the at least one radiation fiber core.

22. The system of claim 12, wherein the rectal balloon comprises a radiation absorbing liquid to reduce radiation delivered to the risk region.

23. The system of claim 21, wherein the risk region is a rectal wall.

* * * * *